United States Patent [19]

Nagumo et al.

[11] Patent Number: 5,637,755
[45] Date of Patent: Jun. 10, 1997

[54] SULFONATE COMPOUND PROCESS FOR PRODUCING THE SAME, AND BLEACH COMPOSITION COMPRISING THE SAME

[75] Inventors: Hiroshi Nagumo; Norio Nishikawa; Toyomi Koike, all of Wakayama; Yukinaga Yokota, Osaka; Hiroyuki Yamada, Tochigi, all of Japan

[73] Assignee: Kao Corporation, Tokyo, Japan

[21] Appl. No.: 553,637

[22] PCT Filed: Jun. 16, 1994

[86] PCT No.: PCT/JP94/00975

§ 371 Date: Dec. 5, 1995

§ 102(e) Date: Dec. 5, 1995

[87] PCT Pub. No.: WO94/29270

PCT Pub. Date: Dec. 22, 1994

[30] Foreign Application Priority Data

Jun. 16, 1993 [JP] Japan ................... 5-144794
Jul. 23, 1993 [JP] Japan ................... 5-182497

[51] Int. Cl.$^6$ .................. C07C 309/12; C07C 303/32; C11D 7/54; D06L 3/02
[52] U.S. Cl. ............... 560/60; 252/186.27; 252/186.29; 252/186.38; 252/186.41; 510/372; 510/375
[58] Field of Search ............... 560/60; 510/372, 510/375; 252/186.27, 186.29, 186.38, 186.41

[56] References Cited

U.S. PATENT DOCUMENTS 5,359,127  10/1994  Reinhardt .................. 560/179
5,384,421  1/1995  Day et al. .................. 554/92

FOREIGN PATENT DOCUMENTS 63-227560  9/1988  Japan.
2-1454  1/1990  Japan.

*Primary Examiner*—Fiona T. Powers
*Attorney, Agent, or Firm*—Birch, Stewart, Kolasch & Birch, LLP

[57] ABSTRACT

To provide a sulfonate represented by the following general formula (1A) which is useful as an organic peracid precursor in bleach compositions for domestic use, a process for producing it, and a bleach composition having no irritative smell, high bleaching power and excellent persistence of the bleaching power during the use:

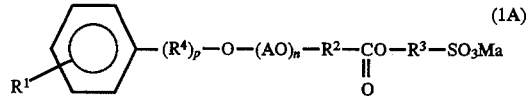

wherein $R^1$ represents a hydrogen atom, an alkyl group having 1 to 10 carbon atoms, etc., $R^2$ represents an alkylene group having 1 to 8 carbon atoms, a phenylene group, etc., $R^3$ represents an alkylene group having 1 to 8 carbon atoms, $R^4$ represents an alkylene group having 1 to 5 carbon atoms, p is 0 or 1, A represents an alkylene group having 2 to 4 carbon atoms, n is 1 to 100, and Ma represents an alkali metal atom. etc.

12 Claims, No Drawings

SULFONATE COMPOUND PROCESS FOR PRODUCING THE SAME, AND BLEACH COMPOSITION COMPRISING THE SAME

BACKGROUND OF THE INVENTION

1. Field of the Invention

The present invention relates to a novel sulfonate useful as an organic peracid precursor for domestic bleach compositions such as a bleach composition for mold stains, a bleach composition for the kitchen and a bleach composition for clothes, and a process for producing the sulfonate. Further, the present invention relates to an oxygen bleach composition free from an irritative smell and having high bleaching power and persistence of bleaching power.

2. Description of the Related Art

Blackish stains on the ceiling, joints between the tiles and plastic wall in a bathroom, garbage strains at the corner of a sink, etc., are caused by a pigment produced by fungi of the genus Cladosporium and the like. Since such blackish stains cannot be removed with only a cleanser or a surfactant, a bleach composition comprising a chlorine bleaching agent such as a hypochlorite which is used in the form of a spray, are now on the market as a product for removing blackish stains.

Although bleach compositions comprising a hypochlorite are excellent in bleaching power, they are very harmful to the eyes and skin and, in particular, those to be used in the form of a spray are unsuitable for removing blackish stains on ceilings, etc. Further, consumers are reluctant to use a bleach composition comprising a hypochlorite in a small bathroom and the like, since it has a strong smell peculiar to a chlorine bleaching agent.

Furthermore, there is a problem that when a bleach composition comprising a hypochlorite is used in combination with an acidic detergent by mistake, a poisonous gas will be formed.

Recently, investigations have been made with respect to oxygen bleach compositions free from such dangers, e.g., a bleach composition comprising hydrogen peroxide or sodium percarbonate, a bleach activator and a peroxydisulfate.

In oxygen bleach compositions, use is usually made of a bleach activator together with a bleaching agent. Examples of the bleach activators include tetraacetylethylenediamine, tetraacetylglycoluril and pentaerythritol tetraacetate. However, such bleach activators have a strong irritative smell, since they form peracetic acid as an active bleach species, and they pose problems when they are practically used.

U.S. Pat. Nos. 4,684,551 (patented on Jan. 6, 1987; assignee: Procter & Gamble Co.), U.S. Pat. No. 4,859,800 (patented on Aug. 22, 1989; assignee: Clorox Co. & Zielske A.G.), 4,956,117 (patented on Sep. 11, 1990; assignee: Clorox Co. & Zielske A.G.) and 5,049,305 (patented on Sep. 17, 1991; assignee: Clorox Co. & Zielske A.G.) disclose compounds represented by the following general formula (a) as organic peracid precursors usable for the bleach compositions:

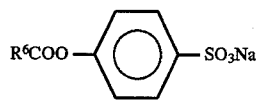
(a)

wherein $R^6$ represents a group represented by the formula:

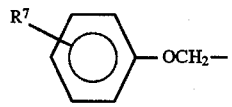

(wherein $R^7$ represents a hydrogen atom or an alkyl group having 1 to 5 carbon atoms) or a group represented by the formula:

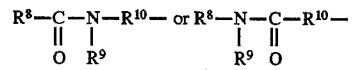

(wherein $R^8$ represents an alkyl, aryl or alkanol group having 1 to about 14 carbon atoms, $R^9$ represents a hydrogen atom or an alkyl, aryl or alkanol group having 1 to about 10 carbon atoms, and $R^{10}$ represents an alkylene, arylene or alkanolene group having 1 to about 14 carbon atoms). The alkanol group is a monovalent group derived from an alkanol represented by the formula: $R-Ar-SO_3M$ (wherein R represents an alkyl group, Ar represents a divalent aromatic group and M represents an aklali metal or hydrogen atom), and the alkanolene group is a divalent group represented by the formula:

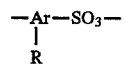

(wherein R represents an alkyl group, and Ar represents a trivalent aromatic group).

However, when the compound represented by the above general formula (a) is used as an organic peracid precursor for achieving a further improved bleaching power in a system containing hydrogen peroxide, etc. and the organic peroxide precursor in high concentrations, an organic peracid formed by the perhydrolysis of the organic peracid precursor is consumed for the oxidation of sodium phenolsulfonate as the leaving group. Therefore, the intended effect cannot be obtained when a bleach composition comprising the compound represented by the above general formula (a) as an organic peracid precursor is used. In addition, the synthesis of the compound represented by the above general formula (a) includes a step of esterification of an acid with an alcohol through dehydration. However, this step is difficult to practice, which causes a problem in the sysnthesis of the compound on an industrial scale.

A literature other than the above patents also discloses the use of a compound of which leaving group is a phenol derivative as the organic peracid precursor. However, the expected effect cannot be obtained when such an organic peracid precursor is used for the same reasons as those in the above-described case wherein an organic peracid precursor, of which leaving group is sodium phenolsulfonate, is used.

Although an organic peracid precursor, of which leaving group is glucose, is also known, the substance which is prepared by an industrially possible esterification reaction of an acid with glucose, had poor physical properties as a solid and was severely colored. Namely, a substance as an organic peracid precursor intended by the inventors could not be obtained from an acid and glucose.

Under these circumstances, an object of the present invention is to provide an organic peracid precursor which does not give out an unpleasant irritative smell under bleaching conditions and which can be easily synthesized on an industrial scale from inexpensive starting materials, and a process for producing it. Another object of the present invention is to provide an oxygen bleach composition being free from the irritative smell and having high bleaching power and persistance of bleaching power.

DISCLOSURE OF THE INVENTION

Summary of the Invention

The present inventors have made extensive investigations for solving the above-described problems under those circumstances. As the result, the present inventors have found that novel sulfonates represented by the following general formulas (1A) or (1B), which have no irritative smell and have excellent bleaching power and bleaching power persistence, are useful as organic peracid precursors for oxygen bleach compositions such as a bleach composition for mold stain, a bleach composition for kitchen and a bleach composition for clothes. The present invention has been completed on the basis of this finding.

Thus, the present invention provides a sulfonate represented by the following general formulas (1A) or (1B):

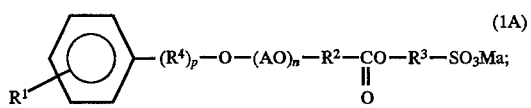

and

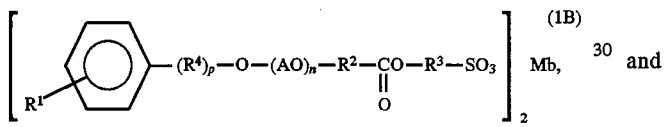

in the formulas (1A) and (1B), $R^1$ represents a hydrogen atom, a linear or branched alkyl group having 1 to 10 carbon atoms, a linear or branched alkenyl group having 2 to 10 carbon atoms or a linear or branched acyl group having 2 to 10 carbon atoms, $R^2$ represents a linear or branched alkylene group having 1 to 8 carbon atoms or a phenylene group which may be substituted by a linear or branched alkyl group having 1 to 5 carbon atoms, $R^3$ represents a linear or branched alkylene group having 1 to 8 carbon atoms, $R^4$ represents a linear or branched alkylene group having 1 to 5 carbon atoms, p represents a number of 0 or 1, A represents an alkylene group having 2 to 4 carbon atoms, n represents a number of 1 to 100, each A may be the same or different from one another, Ma represents an alkali metal atom, an ammonium, an alkylammonium or an alkanolammonium, and Mb represents an alkaline earth metal atom.

In other words, the present invention relates to a sulfonate represented by the following general formula (1):

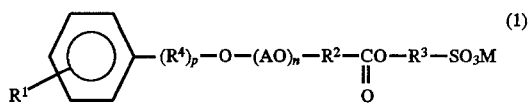

wherein $R^1$ represents a hydrogen atom or a linear or branched, alkyl, alkenyl or acyl group having 1 to 10 carbon atoms, $R^2$ represents a linear or branched alkylene group having 1 to 8 carbon atoms or a phenylene group which may be substituted by a linear or branched alkyl group having 1 to 5 carbon atoms, $R^3$ represents a linear or branched alkylene group having 1 to 8 carbon atoms, $R^4$ represents a linear or branched alkylene group having 1 to 5 carbon atoms, p represents a number of 0 or 1, A represents an alkylene group having 2 to 4 carbon atoms, n represents a number of 1 to 100, nA's may be the same or different from one another, and M represents an alkali metal atom, an alkaline earth metal atom, an ammonium, an alkylammonium or an alkanolammonium.

Further, the present invention provides a process for producing a sulfonate which comprises reacting an ether carbonyl compound represented by the following general formula (2) with a hydroxyalkanesulfonate represented by the following general formulas (3A) or (3B):

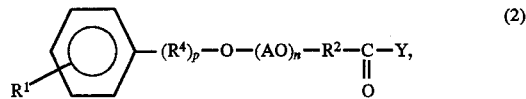

in the formula (2), $R^1$ represents a hydrogen atom, a linear or branched alkyl group having 1 to 10 carbon atoms, a linear or branched alkenyl group having 2 to 10 carbon atoms or a linear or branched acyl group having 2 to 10 carbon atoms, $R^2$ represents a linear or branched alkylene group having 1 to 8 carbon atoms or a phenylene group which may be substituted by a linear or branched alkyl group having 1 to 5 carbon atoms, $R^4$ represents a linear or branched alkylene group having 1 to 5 carbon atoms, p represents a number of 0 or 1, A represents an alkylene group having 2 to 4 carbon atoms, n represents a number of 1 to 100, each A may be the same or different from one another, and Y represents a hydroxyl group, a halogen atom or an alkoxy group having 1 to 3 carbon atoms; and,

and

in the formulas (3A) and (3B), $R^3$ represents a linear or branched alkylene group having 1 to 8 carbon atoms, Ma represents an alkali metal atom, an ammonium, an alkylammonium or an alkanolammonium, and Mb represents an alkaline earth metal atom.

In other words, the present invention relates to a process for producing the above-mentioned sulfonate of the present invention, characterized by reacting an ether carbonyl compound represented by the following general formula (2):

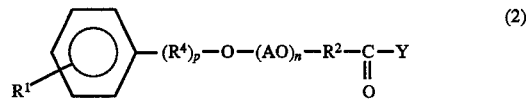

wherein $R^1$ represents a hydrogen atom or a linear or branched alkyl, alkenyl or acyl group having 1 to 10 carbon atoms, $R^2$ represents a linear or branched alkylene group having 1 to 8 carbon atoms or a phenylene group which may be substituted by a linear or branched alkyl group having 1 to 5 carbon atoms, $R^4$ represents a linear or branched alkylene group having 1 to 5 carbon atoms, p represents a number of 0 or 1, A represents an alkylene group having 2 to 4 carbon atoms, n represents a number of 1 to 100, nA's may be the same or different from one another, and Y represents a hydroxyl group, a halogen atom or an alkoxy group having 1 to 3 carbon atoms, with a hydroxyalkanesulfonate represented by the following general formula (3):

wherein $R^3$ represents a linear or branched alkylene group having 1 to 8 carbon atoms, and M represents an alkali metal atom, an alkaline earth metal atom, an ammonium, an alkylammonium or an alkanolammonium.

Furthermore, the present invention provides a bleach composition comprising, based on the total weight of the bleach composition, 0.1 to 98% by weight of (A) hydrogen peroxide or a peroxide capable of forming hydrogen peroxide in an aqueous solution, and 0.002 to 50% by weight of (B) a sulfonate represented by the above general formulas (1A) or (1B).

In other words, the present invention relates a bleaching agent composition characterized by containing:

(A) 0.1 to 98% by weight of hydrogen peroxide or a peroxide which forms hydrogen peroxide in an aqueous solution, and (B) 0.002 to 50% by weight of an organic peracid precursor comprising a sulfonate represented by the above general formula (1), as the indispensable components.

DETAILED DESCRIPTION OF THE INVENTION

Now, the sulfonate represented by the above general formulas (1A) or (1B) will be described. More particularly, the above general formulas (1A) and (1B) will be described.

Examples the linear or branched alkyl group having 1 to 10 carbon atoms of $R^1$ include methyl group, ethyl group, n-propyl group, n-butyl group, n-pentyl group, isopropyl group, isobutyl group, isopentyl group, octyl group and nonyl group. Examples the linear or branched alkenyl group having 2 to 10 carbon atoms of $R^1$ include vinyl group, allyl group and isopropenyl group. Examples of the linear or branched acyl group having 2 to 10 carbon atoms of $R^1$ include acetyl group, propionyl group, butyryl group and valeryl group. Preferred example of the group of $R^1$ includes methyl group.

Examples of the linear or branched alkylene group $R^2$ having 1 to 8 carbon atoms of $R^2$ include methylene group, ethylene group, propylene group, ethylethylene group, trimethylene group, tetramethylene group, hexamethylene group, heptamethylene group and octamethylene group. Examples of the phenylene group which may be substituted by a linear or branched alkyl group having 1 to 5 carbon atoms of $R^2$ include 1,2-phenylene group, 1,4-phenylene group, 2-methyl-1,4-phenylene group, 2-ethyl-1,4-phenylene group, 2-propyl-1,4-phenylene group, 2-butyl-1,4-phenylene group, 2-heptyl-1,4-phenylene group, 2-(1-methylethyl)-1,4-phenylene group, 2-(1-methylpropyl)-1,4-phenylene group and 2-(2-methylbutyl)-1,4-phenylene group. Preferred example of the group of $R^2$ includes methylene group.

Examples of the linear or branched alkylene group having 1 to 8 carbon atoms of $R^3$ include methylene group, ethylene group, propylene group, ethylethylene group, trimethylene group, tetramethylene group, hexamethylene group, heptamethylene group and octamethylene group. Preferred example of the group of $R^3$ includes ethylene group.

Examples of the linear or branched alkylene group $R^4$ having 1 to 5 carbon atoms include methylene group, ethylene group, propylene group and tetramethylene group. Preferred example of the group of $R^4$ includes methylene group.

Examples of the alkylene group having 2 to 4 carbon atoms of A include ethylene group, propylene group, trimethylene group and tetramethylene group.

In the general formulas (1A) and (1B) which represent the sulfonates of the present invention, the n represents the average number of oxyalkylene groups, i.e., the average addition mole number of alkylene oxide. The n is a number of 1 to 100, and preferably a number of 1 to 10. Each oxyalkylene group (AO) may be the same or different from one another. Specific examples of the group represented by [—(AO)$_n$—] include polyoxyethylene group, polyoxypropylene group and polyoxyethylene-polyoxypropylene group.

Examples of the alkali metal atom of Ma include sodium atom and potassium atom, those of the alkylammonium include methylammonium and diethylammonium, and those of the alkanolammonium include monoethanolammonium and triethanolammonium.

Examples of the alkaline earth metal atom of Mb include magnesium atom and calcium atom.

The sulfonate represented by the above general formula (1A) of the present invention can be produced by, for example, reacting an ether carbonyl compound represented by the general formula (2) with a hydroxyalkanesulfonate represented by the general formula (3A) according to the following reaction formula:

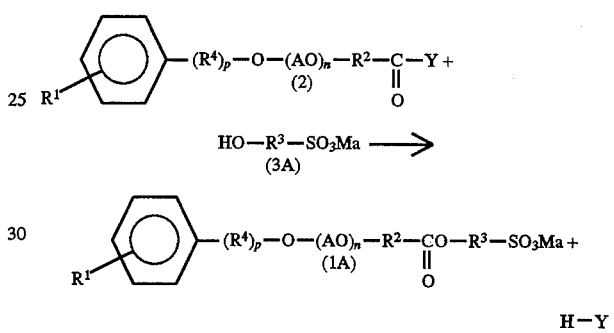

wherein $R^1$, $R^2$, $R^3$, $R^4$, A, Ma, n and p are each as defined above, and Y represents a hydroxyl group, a halogen atom or an alkoxy group having 1 to 3 carbon atoms.

In the above formula, examples of the halogen atom of Y include chlorine atom, fluorine atom, bromine atom and iodine atom, and those of the alkoxy group having 1 to 3 carbon atoms include methoxy group, ethoxy group and propoxy group.

The sulfonate represented by the above general formula (1B) of the present invention can be produced by, for example, reacting an ether carbonyl compound represented by the general formula (2) with a hydroxyalkanesulfonate represented by the general formula (3B) according to the following reaction formula:

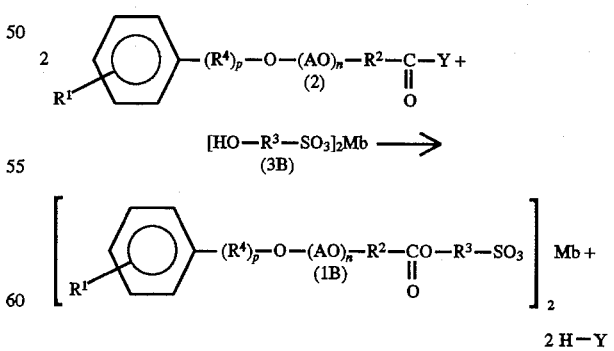

wherein $R^1$, $R^2$, $R^3$, $R^4$, A, Mb, n, p and Y are each as defined above.

The ether carbonyl compounds represented by the general formula (2) to be used in the producing process of the present invention include, for example, organic acids such as 2-phenoxyethoxyacetic acid (⬡—OC$_2$H$_4$OCH$_2$COOH), 2-benzyloxyethoxyacetic acid (⬡—CH$_2$OC$_2$H$_4$OCH$_2$COOH), phenoxypolyoxyethyleneacetic acid (⬡—O(EO)$_n$CH$_2$COOH, n = 1~100), benzyloxypolyoxyethyleneacetic acid (⬡—CH$_2$O(EO)$_n$CH$_2$COOH, n = 1~100), nonylphenoxypolyoxyethyleneacetic acid (C$_9$H$_{19}$—⬡—O(EO)$_n$CH$_2$COOH, n = 1~100), phenoxypolyoxyethylenepropionic acid (⬡—O(EO)$_n$CH$_2$CH$_2$COOH, n = 1~100), benzyloxypolyoxyethylenepropionic acid (⬡—CH$_2$O(EO)$_n$CH$_2$CH$_2$COOH, n = 1~100), and nonylphenoxypolyoxyethylenepropionic acid (C$_9$H$_{19}$—⬡—O(EO)$_n$CH$_2$CH$_2$COOH, n = 1~100), mixed acids of two or more these organic acids, acyl halides (i.e., acid halides) corresponding to the above organic acids, mixtures of two or more these acyl halides, lower alcohol esters of the above organic acids and mixtures of two or more these esters.

The ether carbonyl compounds (2) produced by any process are usable in the present invention.

For example, an organic acid (2-a) of the general formula (2) wherein Y represents a hydroxyl group can be obtained by reacting a corresponding glycol ether salt (4) with a halogen compound (5) according to the following reaction formula:

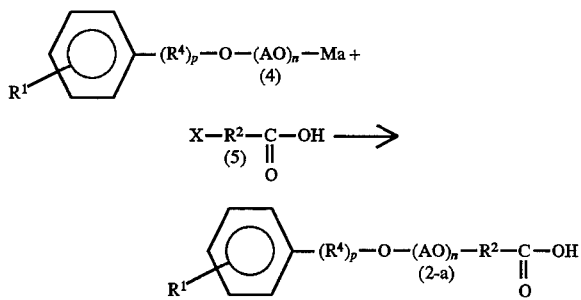

wherein $R^1$, $R^2$, $R^4$, A, Ma, n and p are each as defined above, and X represents a halogen atom.

An organic acid (2-b) of the general formula (2) wherein Y represents a hydroxyl group and $R^2$ represents a methylene group can also be obtained by oxidizing a (poly) oxyethylene ether (6) with oxygen or air in the presence of a platinum or palladium catalyst according to the following reaction formula:

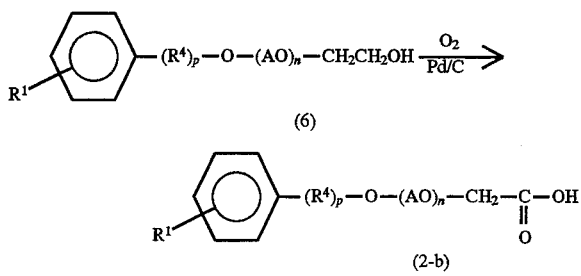

wherein $R^1$, $R^4$, A, n and p are each as defined above.

Further, an acyl halide (2-c) of the general formula (2) wherein Y represents a halogen atom and a lower alcohol ester (2-d) of the general formula (2) wherein Y represents an alkoxyl group having 1 to 3 carbon atoms can be produced from the organic acid (2-a) or (2-b) obtained as described above by a known process.

Examples of the hydroxyalkanesulfonate represented by the general formula (3A) to be used in the producing process of the present invention include sodium, potassium, ammonium, methylammonium, diethylammonium and triethanolammonium salts of hydroxyalkanesulfonic acids such as 2-hydroxyethane-1-sulfonic acid (isethionic acid), 2-hydroxypropane-1-sulfonic acid, 1-hydroxypropane-2-sulfonic acid, 1-hydroxybutane-2-sulfonic acid and 2-hydroxypentane-1-sulfonic acid.

Examples of the hydroxyalkanesulfonate represented by the general formula (3B) to be used in the producing process of the present invention include calcium salts of hydroxyalkanesulfonic acids such as 2-hydroxyethane-1-sulfonic acid (isethionic acid), 2-hydroxypropane-1-sulfonic acid, 1-hydroxypropane-2-sulfonic acid, 1-hydroxybutane-2-sulfonic acid and 2-hydroxypentane-1-sulfonic acid.

In the producing process of the present invention, the ether carbonyl compound (2) is used in an amount of preferably 0.5 to 3 mol, particularly 0.8 to 2 mol, per mole of the hydroxyalkanesulfonate (3A). Meanwhile, in the producing process of the present invention, the ether carbonyl compound (2) is used in an amount of preferably 1 to 6 mol, particularly 1.6 to 4 mol, per mole of the hydroxyalkanesulfonate (3B).

Although a solvent is not always necessitated for this reaction, it may be used. The solvent usable herein may be any solvent so far as it is inert to the starting materials and the reaction product. In the reaction of the organic acid (2-a) or (2-b) with the hydroxyalkanesulfonate (3A) or (3B), particularly, it is preferred to use an inert organic solvent capable of forming an azeotropic mixture with water to facilitate the dehydration. Examples of such an inert organic solvent include benzene, cyclohexane, toluene, xylene, ethylbenzene and monochlorobenzene. They can be used either singly or in the form of a mixture of two or more of them.

The reaction temperature is preferably 70° to 250° C., particularly 80° to 220° C.

Although the reaction proceeds sufficiently in the absence of any catalyst in practicing the producing process of the present invention, the reaction can be efficiently conducted by using an esterification catalyst which is ordinary used in esterification. Among such esterification catalysts, acidic catalysts include, for example, sulfuric acid, hydrochloric acid and p-toluenesulfonic acid, and basic catalysts include, for example, alkali metal hydroxides and alkali metal alcoholates. The esterification catalyst is used in an amount of preferably about 0.1 to 5% by weight based on the whole amount of the reaction system.

The progress of the reaction in the producing process of the present invention can be confirmed by determining the quantity of water or alcohol distilled off the reaction system. Specially, the hydroxyl value is determined, or the quantity of the hydroxyalkane sulfonate is determined by liquid chromatography. In the reaction mixture thus obtained, unreacted ether carbonyl compound (2) or, unreacted hydroxyalkanesulfonate (3A) or (3B) depending on the reaction molar ratio, and further the solvent used and the catalyst used, in addition to the intended sulfonate of the present invention represented by the general formula (1A) or (1B), are contained. Although the reaction mixture thus obtained can also be used as it is depending on the purpose, a highly pure product is obtained by further purifying it.

Examples of the method for removing the reaction solvent from the reaction mixture include filtration and distillation under reduced pressure; and those for removing unreacted starting materials and the catalyst include crystallization, reprecipitation and dialysis.

For instance, in the case that the objective compound is sodium salt of 2-sulfoethyl 2-phenoxyethoxyacetate [a compound of the formula (1) wherein $R^1$ represents H, $R^2$ represents $CH_2$, $R^3$ represents $C_2H_4$, A represents $C_2H_4$, Ma represents Na, n represents 1, and p represents O], the compound having a high purity can be obtained by reacting 2-phenoxyethoxyacetic acid with sodium 2-hydroxyethylsulfonate (sodium isethionate) in the absence of any catalyst without using any solvent, adding acetone to the reaction mixture thus obtained to wash the reaction product, and filtering the mixture of the reaction mixture and acetone.

Next, the description will now be made on the bleach composition of the present invention.

Examples of the peroxide capable of forming hydrogen peroxide in the aqueous solution as component (A) of the bleach composition according to the present invention, include sodium percarbonate, sodium tripolyphosphate/hydrogen peroxide adduct, sodium pyrophosphate/hydrogen peroxide adduct, urea/hydrogen peroxide adduct, $4Na_2SO_4 \cdot 2H_2O_2 \cdot NaCl$, sodium perborate monohydrate, sodium perborate tetrahydrate, sodium persilicate, sodium peroxide and calcium peroxide. Among them, sodium percarbonate, sodium perborate monohydrate and sodium perborate tetrahydrate are particularly preferred.

Component (A) is contained in an amount of from 0.1 to 98% by weight in the bleach composition of the present invention. When hydrogen peroxide is used as component (A), the amount thereof is desirably 0.1 to 30% by weight, more desirably 0.5 to 6% by weight, based on the total weight of the composition. When a peroxide which forms hydrogen peroxide in the aqueous solution is used as component (A), the amount thereof is desirably 0.1 to 98% by weight, more desirably 0.5 to 70% by weight, based on the total weight of the composition.

When the amount of component (A) in the bleach composition of the present invention is below 0.14 by weight, the amount of hydrogen peroxide to be reacted with component (B) in the aqueous solution is insufficient for obtaining a sufficient bleaching effect. On the contrary, when it exceeds 98% by weight, the amount of component (B) becomes insufficient for obtaining a sufficient bleaching effect.

In the bleach composition of the present invention, the sulfonate (the organic peracid precursor) represented by the above general formula (1A) or (1B) as component (B) is contained in an amount of from 0.002 to 50% by weight based on the total weight of the composition. When the amount of component (B) is below 0.002% by weight, it is insufficient for obtaining a sufficient bleaching effect and, on the contrary, even when it exceeds 50% by weight, the bleaching effect is no more improved, which is economically disadvantageous.

The amounts of components (A) and (B) are selected in the range that the component (A)/component (B) (weight ratio) becomes preferably 50/1 to 1/10, particularly 20/1 to 1/5, from the viewpoint of the improvement of the bleaching power. When the above weight ratio exceeds 50/1, the proportion of the concentration of the organic peracid to be formed to the hydrogen peroxide concentration become so low as to possibly impair the bleaching power improving effect, unfavorably. On the contrary, when the above weight ratio is below 1/10, the excess unreacted organic peracid precursor remains in the reaction system in some cases, which is economically disadvantageously.

In the bleach composition of the present invention, the components are contained in such amounts that the available oxygen concentration at the time of use will be 0.01 to 5%. When the available oxygen concentration is below 0.01%, the bleaching power is low unfavorably and, on the contrary, even when it exceeds 5%, the effect is no more increased and such a high concentration is economically disadvantageous.

Surfactant (C) may be further incorporated into the bleach composition of the present invention. Since surfactant (C) improves the penetration of the aqueous solution of the bleach composition into stains, a high bleaching power can be obtained when a bleach composition containing a surfactant is used. The weight ratio of the total weight of the above components (A) and (B) to the weight of the surfactant as component (C), i.e., [components (A)+(B)]/component (C), is in the range of preferably from 99.9/0.1 to 50/50, particularly from 99/1 to 70/30, from the viewpoints of the penetration the aqueous solution of the bleach composition into stains, the stability of the organic peracid and the bleaching and deterging effect. The amount of the surfactant as component (C) is desirably 0.01 to 20% by weight, particularly 0.1 to 10% by weight, based on the total weight of the bleach composition which is prepared by adding the surfactant. Also in this case, the amount of each of the above components (A) and (B) to be incorporated is in the same range as one described above.

Examples of the surfactant as component (C) to be used in the present invention include nonionic surfactants such as alkyl glycosides, polyoxyethylene alkyl ethers, sorbitan/fatty acid esters, polyoxyethylene sorbitan/fatty acid esters, polyoxyethylene/fatty acid esters, oxyethylene oxypropylene block polymers (Pluronic), fatty acid monoglycerides and amine oxides; anionic surfactants such as soaps, alkylsulfates, alkylbenzenesulfonates, polyoxyethylene alkylsulfate salts, sulfosuccinic diester salts and N-alkyl amino acid type surfactants; cationic surfactants such as mono- or dialkylamines, polyoxyethylene adducts of them and mon- or di(long-chain alkyl) quaternary ammonium salts; and amphoteric surfactants such as carbobetaines, sulfobetaines and hydroxysulfobetaines. Among them, anionic surfactants such as alkylbenzenesulfonates and soaps are particularly excellent from the viewpoint of the deterging power.

The bleaching effect can be further improved by incorporating a pH regulator into the bleach composition of the present invention to be the pH of the stock solution or the aqueous solution of the composition 5 to 13, preferably 9 to 11. When the pH of the stock solution or the aqueous solution of the composition is below 5, the reactivity of the components (A) and (B) is reduced to lower the yield of the organic peracid which is the active ingredient and, on the contrary, when the pH is above 13, the stability of the obtained organic peracid is reduced.

Examples of the pH regulator include alkali metal hydroxides such as sodium hydroxide and potassium hydroxide; amine derivatives such as ammonium hydroxide and mono-, di- and triethanolamines; alkali metal carbonates such as sodium carbonate and potassium carbonate; other carbonates such as ammonium carbonate; alkali metal silicates such as sodium silicate and potassium silicate; and other silicates such as ammonium silicate. Further, if necessary, an alkali metal sulfate such as sodium sulfate, potassium sulfate and lithium sulfate; ammonium sulfate; an alkali metal hydrogencarbonate such as sodium hydrogencarbonate, potassium hydrogencarbonate and lithium hydrogencarbonate; or ammonium hydrogencarbonate can be used in the bleach composition of the present invention.

Furthermore, if necessary, a solubilizer such as sodium p-toluenesulfonate, sodium xylenesulfonate, sodium alkenylsuccinates and urea; a thickener; a penetrant; a suspending agent such as clay; an abrasive; a chelating agent; a pigment; a dye; a fragrance, etc. can be used in the bleach composition of the present invention.

Preferred amounts (based on the total weight of the composition) of the above-described optional components which can be incorporated into the bleach composition of the present invention are as follows:

pH regulator 0.1 to 30% by weight
solubilizer 0.1 to 10% by weight
thickener 0.1 to 5% by weight
penetrant 0.1 to 10% by weight
suspending agent 0.1 to 10% by weight
abrasive 0.1 to 20% by weight
chelating agent 0.1 to 10% by weight
pigment, dye, fragrance, etc. suitable amount When it is intended to obtain the bleach composition of the present invention in liquid form, the intended bleach composition can be prepared by adding water to the above-described indispensable components and optional components. The amount of the water to be incorporated is not particularly limited.

The bleach composition of the present invention is usable in either the one-pack form containing both components (A) and (B) or the two-pack form wherein the components (A) and (B) are in separate packs. From the viewpoint of easiness of use, however, the one-pack form is preferred. In this case, it is desirable to use a powdery peroxide capable of forming hydrogen peroxide in the aqueous solution as component (A), since it is difficult to use liquid hydrogen peroxide as component (A) from the viewpoint of the storability. The user dissolves a powdery or solid product of the present invention in water before use and sprinkles or sprays the obtained aqueous solution on the surface of the object to effect bleach treatment.

In addition to the one-pack form, the two-pack form is possible, wherein components (A) and (B) are separately packed. Optional components and water can be incorporated into each pack. In using the two-pack form composition, the user breaks each pack and mixes the contents each other (by adding water, if necessary) immediately before the use to form a solution, slurry or paste, and immediately sprinkles or sprays it on the surface of the object to effect bleach treatment.

The novel sulfonate of the present invention is an excellent organic peracid precursor which is incorporated into oxygen bleach composition, since it is free from the irritative smell, and reacts with hydrogen peroxide to form an organic peracid to thereby exhibit a high bleaching power. Therefore, the bleach composition containing the sulfonate is very useful as a bleach composition for domestic use such as a bleach composition for mold stain, a bleach composition for kitchen and a bleach composition for clothes.

Further, according to the present invention, an oxygen bleach composition free from the irritative smell, having a high bleaching power, the persistence of the bleaching power of at least about 30 min during the use and a high penetration into the stains can be obtained.

EXAMPLES

The present invention will be described hereinafter in greater detail with reference to Examples. The present invention is not restricted to them.

Example 1

294 g (1.5 mol) of 2-phenoxyethoxyacetic acid and 148 g (1.0 mol) of sodium isethionate were fed into a 1-l flask equipped with a stirrer, a thermometer, a nitrogen gas-inlet tube and a reflux condenser having a water separator. The contents in the flask were heated with an external heater while stirring in a nitrogen gas atmosphere. Although the distillation of water formed by the reaction was observed during the temperature elevation, the temperature was finally elevated to 200° C. During reacting at this temperature for 10 hours, the quantity of distilled water reached 17 ml, and then the distillation ceased. Therefore, heating was stopped and the flask was cooled to obtain 424 g of a light yellow paste. Then, the reaction product (paste) was added to 2,000 ml of acetone, and the resultant mixture was stirred and then filtered to separate the solid from the liquid. This washing operation was repeated three times in total and then acetone was distilled off by drying the residue on the filter under reduced pressure to obtain 290 g (yield: 89% based on the calculated amount) of sodium salt of 2-sulfoethyl 2-phenoxyethoxyacetate represented by the following formula (7) in the form of a white solid:

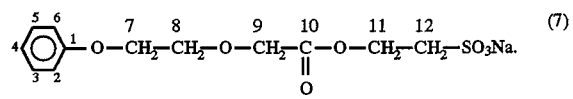

The result of $^{13}$C-NMR analysis thereof are shown in Table 1.

Further, the result of elementary analysis thereof are shown in Table 2.

TABLE 1

| Position of carbon | δ (ppm) |
|---|---|
| 1 | 157.5 |
| 2, 6 | 114.4 |
| 3, 5 | 129.4 |
| 4 | 121.1 |
| 7 | 67.6 |
| 8 | 73.7 |
| 9 | 69.9 |
| 10 | 170.5 |
| 11 | 61.0 |
| 12 | 49.8 |

TABLE 2

|  | C (%) | H (%) | S (%) | Na (%) |
|---|---|---|---|---|
| Found | 44.2 | 4.6 | 9.5 | 7.0 |
| Calculated | 44.2 | 4.6 | 9.8 | 7.1 |

Example 2

360 g (1.5 mol) of a compound (average addition mol number of ethylene oxide: 2 mol; average molecular weight: 239.9) represented by the formula (8):

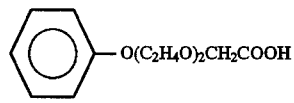  (8)

and 148 g (1.0 mol) of sodium isethionate were fed into a 1-l flask equipped with a stirrer, a thermometer, a nitrogen gas-inlet tube and a reflux condenser having a water separator. The contents in the flask were heated with an external heater while stirring in a nitrogen gas atmosphere. Although the distillation of water formed by the reaction was observed during the temperature elevation, the temperature was finally elevated to 200° C. During reacting at this temperature for 10 hours, the quantity of distilled water reached 17 ml, and then the distillation ceased. Therefore, heating was stopped and the flask was cooled to obtain 490 g of a yellow paste. Then, the reaction product (paste) was added to 2,000 ml of acetone, and the resultant mixture was stirred and then filtered to separate the solid from the liquid. This operation was repeated three times in total and then acetone was distilled off by drying the residue on the filter under reduced pressure to obtain 344 g (yield: 93%) of a compound represented by the following formula (9) in the form of a white solid:

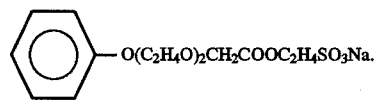  (9)

The product had an ester value of 151 mg KOH/g, which coincided with the theoretical value. In the IR determination of this product, an absorption assignable to ester was observed at 1750 cm$^{-1}$ and a broad absorption assignable to sulfonic acid was observed at 1200 cm$^{-1}$.

Example 3

449 g (1.5 mol) of a compound (average addition mol number of ethylene oxide: 3 mol; average molecular weight: 299.5) represented by the formula (10):

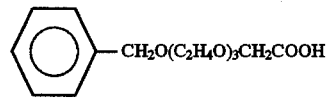  (10)

and 148 g (1.0 mol) of sodium isethionate were fed into a 1-l flask equipped with a stirrer, a thermometer, a nitrogen gas-inlet tube and a reflux condenser having a water separator. The contents in the flask were heated with an external heater while stirring in a nitrogen gas atmosphere. Although the distillation of water formed by the reaction was observed during the temperature elevation, the temperature was finally elevated to 200° C. During reacting at this temperature for 10 hours, the quantity of distilled water reached 17 ml, and then the distillation ceased. Therefore, heating was stopped and the flask was cooled to obtain 578 g of a yellow paste. Then, the reaction product (paste) was added to 2,000 ml of acetone, and the resultant mixture was stirred and then filtered to separate the solid from the liquid. This operation was repeated three times in total and then acetone was distilled off by drying the residue on the filter under reduced pressure to obtain 391 g (yield: 91%) of a compound represented by the following formula (11) in the form of a white solid:

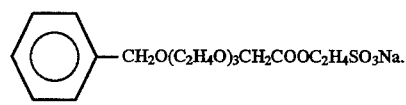  (11)

The product had an ester value of 130 mg KOH/g, which coincided with the theoretical value. In the IR determination of this product, an absorption assignable to ester was observed at 1748 cm$^{-1}$ and a broad absorption assignable to sulfonic acid was observed at 1200 cm$^{-1}$.

Comparative Example 57 g (0.25 mol) of disodium phenolsulfonate and 500 mol of dimethylformamide were fed into a 1-l flask equipped with a stirrer, a thermometer and a nitrogen gas-inlet tube. The temperature was elevated to 70° C. while the contents in the flask were stirred in a nitrogen gas atmosphere. 50 g (0.29 mol) of phenoxyacetyl chloride was dropwise added at that temperature. After stirring the contents in the flask at that temperature for 3 hours, the pressure in the system was reduced to 25 Torr at that temperature and excess phenoxyacetyl chloride and dimethylformamide were distilled off to obtain a mixture in the form of a slurry. This mixture was added to 1,000 ml of acetone and the resultant mixture was stirred to form a white precipitate. By filtration, the white precipitate was separated and washed with 500 ml of acetone three times to obtain 62 g of sodium salt of p-sulfophenyl phenoxyacetate represented by the following formula (12):

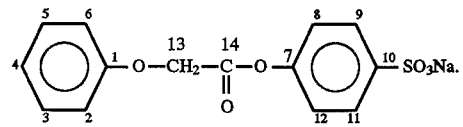  (12)

The result of $^{13}$C-NMR analysis thereof are shown in Table 3.

TABLE 3

| Position of carbon atom | δ (ppm) |
|---|---|
| 14 | 167.8 |
| 1 | 157.5 |
| 7 | 150.0 |
| 10 | 145.8 |
| 3, 5 | 129.6 |
| 9, 11 | 127.1 |
| 4 | 121.4 |
| 8, 12 | 121.1 |
| 2, 6 | 114.6 |
| 13 | 64.6 |

Example 4

An aqueous solution of a bleach composition (available oxygen concentration: about 1.41%) containing 10% by weight of the sulfonate of the present invention produced in each of Examples 1 to 3 or tetraacetylethylenediamine ordinarily used as an organic peracid precursor and 3% by weight of hydrogen peroxide was prepared and subjected to the bleaching power test for mold stain and the smell test by the methods which will be described below. The results are given in Table 4.

Bleaching power test for mold stain:

Model mold plates were prepared by inoculating plastic plates (made of ABS resin) with *Cladosporium herbarium* and incubating at 30° C. for 14 days. Each of the plates was kept horizontal, and then 40 µl of each of the aqueous solutions of the bleach compositions was dropwise added on the surface thereof where the mold has been increased. After leaving the model mold plate to stand for 30 min followed by washing with water and drying with air, the lightness (L value) was determined with a colorimeter 1001DP (a product of Nippon Denki Kogyo Co., Ltd.). The L value of the plastic plate was 92.4 and that of the model mold plate was 65 to 75. The higher the value, the higher the bleaching power.

Smell test:

The smell of the aqueous solution of the bleaching composition was tested by the organoleptic test by ten panelists.

o: neither irritative smell nor bad smell,
x: irritatives smell or bad smell.

solution of the bleach composition. After 10 min, the black tea-stained cloths bleached were taken out from the aqueous solution of the bleach composition, washed with water and dried. Reflectances of bleached and dried black tea-stained cloths, black tea-stained cloths before bleaching and white cloths before staining were each measured, and the rate of bleaching was calculated according to the following formula:

$$\text{rate of bleaching (\%)} = \frac{\text{reflectance of black tea-stained cloth after bleaching} - \text{reflectance of black tea-stained cloth before bleaching}}{\text{reflectance of white cloth} - \text{reflectance of black tea-stained cloth before bleaching}} \times 100.$$

The higher the value, the higher the bleaching power.

The reflectance was determined by the use of NDR-1001DP, mfd. by Nippon Denki Kogyo Co., Ltd. with a 460 nm filter.

Preparation method of black tea-stained cloths:

80 g of commercially available black tea leaf (mfd. by Nitto Black Tea Co., Ltd., yellow package) was added to 3 l of deionized water and the obtained mixture was boiled for

TABLE 4

| | | Org. peracid precursor | L value | Smell |
|---|---|---|---|---|
| Invention Product | Ex. 1 |  —OC$_2$H$_4$OCH$_2$COOC$_2$H$_4$SO$_3$Na | 92 | o |
| | Ex. 2 |  —O(C$_2$H$_4$O)$_2$CH$_2$COOC$_2$H$_4$SO$_3$Na | 92 | o |
| | Ex. 3 |  —CH$_2$O(C$_2$H$_4$O)$_3$CH$_2$COOC$_2$H$_4$SO$_3$Na | 91 | o |
| Control Product | | tetraacetylethylenediamine | 91 | x |

Example 5

An aqueous solution of a bleach composition (available oxygen concentration: about 1.22%) containing 10% by weight of the sulfonate of the present invention produced in each of Examples 1 to 3 or tetraacetylethylenediamine ordinarily used as an organic peracid precursor, 10% by weight of sodium percarbonate and 2% by weight of sodium dodecyl sulfate was prepared, and subjected to the bleaching power test for cloths stained with black tea by the method which will be described below and the smell test. The smell test was effected by the method described in Example 4. The results are given in Table 5.

Bleaching power test for cloth stained with black tea:

The cloths (8 cm×8 cm) prepared by the method which will be described below were immersed in the aqueous about 15 minutes. The resulting tea containing black tea leaves were filtered through a desized bleached cotton cloth. The tea thus obtained was poured into a pan and a cotton shirting cloth #2003 was immersed in the tea. After boiling the tea for about 15 minutes, the pan containing the tea and the cotton shirting cloth #2003 was taken off the fire and allowed to stand for about 2 hours. The resulting cotton shirting cloth #2003 was taken out from the tea, spontaneously dried, washed until the washings became colorless, dehydrated and pressed to give a test piece (black tea-stained cloth).

TABLE 5

| | Org. peracid precursor | Bleaching rate (%) | Smell |
|---|---|---|---|
| Invention Product | Ex. 1  —OC$_2$H$_4$OCH$_2$COOC$_2$H$_4$SO$_3$Na | 86.2 | o |
| | Ex. 2  —O(C$_2$H$_4$O)$_2$CH$_2$COOC$_2$H$_4$SO$_3$Na | 86.4 | o |
| | Ex. 3  —CH$_2$O(C$_2$H$_4$O)$_3$CH$_2$COOC$_2$H$_4$SO$_3$Na | 84.2 | o |
| Control Product | tetraacetylethylenediamine | 81.4 | x |

Example 6

The bleach compositions listed in Table 6 were prepared. They were evaluated with respect to the bleaching power for mold stain and the smell thereof by the same methods as those in Example 4. The results are given in Table 6.

It will be apparent from the results in Table 6 that Comparative Product. No. 12 has a bad smell and is unacceptable for use. The organic peracid precursor obtained in Comparative Example and used for Comparative Product No. 13 contains sodium phenolsulfonate as the leaving group and has a poor bleaching performance.

The Invention Product Nos. 1 to 11 has no irritative smell, an excellent bleaching performance and a high persistence of the bleaching power. Invention Product Nos. 4 to 9 containing a surfactant exhibit excellent bleaching effect more than those of Invention Product Nos. 1 to 3, 10 and 11 containing no surfactant, since the penetration of each of the aqueous solutions of the bleach compositions into the stain was improved.

TABLE 6

| | | | Invention Product | | | | | | | | | | | Comp. Product | |
|---|---|---|---|---|---|---|---|---|---|---|---|---|---|---|---|
| | | | 1 | 2 | 3 | 4 | 5 | 6 | 7 | 8 | 9 | 10 | 11 | 12 | 13 |
| Component (wt. %) | (A) | sodium percarbonate | 10 | 10 | 10 | 10 | 10 | 10 | 10 | 10 | 10 | 10 | 10 | 10 | 10 |
| | (B) org. peracid precursor*1 | compd. of Ex. 1 | 10 | | | 10 | | | 10 | 7 | 7 | | | | |
| | | compd. of Ex. 2 | | 10 | | | 10 | | | | | 7 | | | |
| | | compd. of Ex. 3 | | | 10 | | | 10 | | | | | 7 | | |
| | | tetraacetyl-ethylenediamine | | | | | | | | | | | | 10 | |
| | | compd. of Comp. Ex. | | | | | | | | | | | | | 10 |
| | sodium hydroxide | | | | | 5 | 5 | 5 | 5 | 5 | 5 | | | 5 | 5 |
| | AS*2 | | | | | 5 | 5 | 5 | 5 | 3 | 3 | | | 5 | 5 |
| | Dequest 2010*3 | | | | | | | | 0.5 | | 0.5 | | | | |
| | sodium p-toluenesulfonate | | | | | | | | 0.5 | | 0.5 | | | | |
| | water | | 80 | 80 | 80 | 70 | 70 | 70 | 69 | 75 | 74 | 83 | 83 | 70 | 70 |
| Evaluation of Performance | bleaching power for mold stain (L value) | after 5 min | 89 | 89 | 88 | 91 | 92 | 91 | 92 | 90 | 91 | 87 | 86 | 90 | 82 |
| | | after 30 min | 87 | 88 | 87 | 89 | 91 | 89 | 91 | 89 | 90 | 85 | 85 | 88 | 75 |
| | smell (the no. of persons) | o | 10 | 10 | 9 | 10 | 10 | 9 | 10 | 10 | 9 | 9 | 10 | 0 | 9 |
| | | x | 0 | 0 | 1 | 0 | 0 | 1 | 0 | 0 | 1 | 1 | 0 | 10 | 1 |

Notes)

*1 Compd. of Ex. 1:  —OC$_2$H$_4$OCH$_2$COOC$_2$H$_4$SO$_3$Na

TABLE 6-continued

|  | Invention Product | | | | | | | | | | | Comp. Product | |
|---|---|---|---|---|---|---|---|---|---|---|---|---|---|
|  | 1 | 2 | 3 | 4 | 5 | 6 | 7 | 8 | 9 | 10 | 11 | 12 | 13 |

Compd. of Ex. 2: ⌬—O(C₂H₄O)₂CH₂COOC₂H₄SO₃Na

Compd. of Ex. 3: ⌬—CH₂O(C₂H₄O)₃CH₂COOC₂H₄SO₃Na

Compd. of Comp. Ex.: ⌬—O—CH₂—C(=O)—O—⌬—SO₃Na

*2 AS: sodium alkyl ($C_{12}$ to $C_{14}$) sulfate,
*3 Dequest 2010: 1-hydroxyethylidene-1,1-diphosphonic acid (a product of Monsanto).

Example 7

The bleach compositions listed in Table 7 were prepared. They were subjected to the bleaching power test for stains of tea incrustations by the method which will be described below and the smell test by the method described in Example 4. The results are given in Table 7.

Bleaching power test for stains of tea incrustations:

In each of the bleach compositions was soaked a teacup (made of melamine resin) stained with tea incrustations for an hour. After the teacup was washed with water and dried, the bleaching power for stains of tea incrustations was evaluated on the basis of the following criteria.
(Criteria for evaluation)

Essentially no tea incrustations remained . . . o

Some tea incruscations remained . . . Δ

The tea incrustations were scarcely removed . . . x

TABLE 7

|  |  |  | Invention Product | | | Comp. Product | |
|---|---|---|---|---|---|---|---|
|  |  |  | 1 | 2 | 3 | 4 | 5 |
| Component (wt. %) | (A) | sodium percabonate | 10 | 10 | 10 | 10 | 10 |
|  | (B) org. peracid precursor | compd. of Ex. 1 | 10 |  |  |  |  |
|  |  | compd. of Ex. 2 |  | 10 |  |  |  |
|  |  | compd. of Ex. 3 |  |  | 10 |  |  |
|  |  | tetraacetylethylene diamine |  |  |  | 10 |  |
|  |  | water | 80 | 80 | 80 | 80 | 90 |
| Evaluation of Performance |  | bleaching power for stains of tea incrustations | o | o | o | o | Δ |
|  |  | smell | o | o | o | x | o |

We claim:

1. A sulfonate represented by the following general formulas (1A) or (1B):

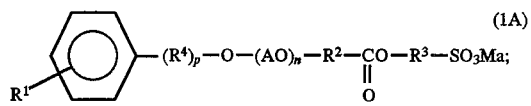

and

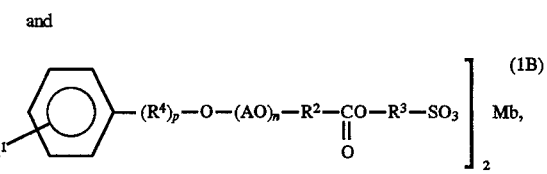

in the formulas (1A) and (1B), $R^1$ represents a hydrogen atom, a linear or branched alkyl group having 1 to 10 carbon atoms, a linear or branched alkenyl group having 2 to 10 carbon atoms or a linear or branched acyl group having 2 to 10 carbon atoms, $R^2$ represents a linear or branched alkylene group having 1 to 8 carbon atoms or a phenylene group which may be substituted by a linear or branched alkyl group having 1 to 5 carbon atoms, $R^3$ represents a linear or branched alkylene group having 1 to 8 carbon atoms, $R^4$ represents a linear or branched alkylene group having 1 to 5 carbon atoms, p represents a number of 0 or 1, A represents an alkylene group having 2 to 4 carbon atoms, n represents a number of 1 to 100, each A may be the same or different from one another, Ma represents an alkali metal atom, an ammonium, an alkylammonium or an alkanolammonium, and Mb represents an alkaline earth metal atom.

2. The sulfonate according to claim 1, wherein n is 1 to 10.

3. The sulfonate according to claim 1, wherein AO is a polyoxyethylene group, a polyoxypropylene group or a polyoxyethylene-polyoxypropylene group.

4. A process for producing a sulfonate which comprises reacting an ether carbonyl compound represented by the following general formula (2) with a hydroxyalkanesulfonate represented by the following general formulas (3A) or (3B):

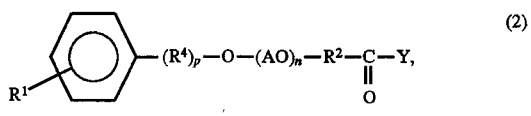

in the formula (2), $R^1$ represents a hydrogen atom, a linear or branched alkyl group having 1 to 10 carbon atoms, a linear or branched alkenyl group having 2 to 10 carbon atoms or a linear or branched acyl group having 2 to 10 carbon atoms, $R^2$ represents a linear or branched alkylene group having 1 to 8 carbon atoms or a phenylene group which may be substituted by a linear or branched alkyl group having 1 to 5 carbon atoms, $R^4$ represents a linear or branched alkylene group having 1 to 5 carbon atoms, p represents a number of 0 or 1, A represents an alkylene group having 2 to 4 carbon atoms, n represents a number of 1 to 100, each A may be the same or different from one another, and Y represents a hydroxyl group, a halogen atom or an alkoxy group having 1 to 3 carbon atoms; and,

 (3A)

or

 (3B), in the formulas (3A) and (3B), $R^3$ represents a linear or branched alkylene group having 1 to 8 carbon atoms, Ma represents an alkali metal atom, an ammonium, an alkylammonium or an alkanolammonium, and Mb represents an alkaline earth metal atom.

5. A bleach composition comprising, based on the total weight of the bleach composition, 0.1 to 98% by weight of (A) hydrogen peroxide or a peroxide capable of forming hydrogen peroxide in an aqueous solution, and 0.002 to 50% by weight of (B) the sulfonate as claimed in claim 1.

6. The bleach composition as claimed in claim 5 which further contains a surfactant (C), wherein the weight ratio of the total weight of the above components (A) and (B) to the weight of component (C), is from 99.9/0.1 to 50/50.

7. The bleach composition according to claim 5, wherein component (2) is selected from the group consisting of sodium percarbonate, sodium tripolyphosphate/hydrogen peroxide adduct, sodium pyrophosphate/hydrogen peroxide adduct, urea/hydrogen peroxide adduct, $4Na_2SO_4 \cdot 2H_2O_2 \cdot NaCl$, sodium perborate monohydrate, sodium perborate tetrahydrate, sodium persilicate, sodium peroxide and calcium peroxide.

8. The bleach composition according to claim 5, wherein said component (A) is present in an amount of 0.1 to 30% by weight based on the total weight of the composition.

9. The bleach composition according to claim 5, wherein said component (A) is a hydrogen peroxide and is present in an amount of 0.5 to 6% by weight, based on the total weight of the composition.

10. The bleach composition according to claim 5, wherein said component (A) is a peroxide which forms hydrogen peroxide in aqueous solution and is present in an amount of 0.5 to 70% by weight based on the total weight of the composition.

11. The bleach composition according to claim 5, wherein the amount of component (A) to component (B) is present is a weight ratio of 20/1 to 1/5.

12. The bleach composition according to claim 6, wherein the weight ratio of component (A) and component (B)/component (C) is in the range of 99/1 to 70/30.

* * * * *